United States Patent [19]

Robson

[11] Patent Number: 5,752,822
[45] Date of Patent: May 19, 1998

[54] APPARATUS FOR RELIEVING UPPER AIRWAY DISORDERS AND RELATED PROBLEMS

[76] Inventor: Farrand C. Robson, 5510 Ray Nash Dr., Gig Harbor, Wash. 98335

[21] Appl. No.: 816,414

[22] Filed: Mar. 13, 1997

[51] Int. Cl.⁶ .................................................. A61C 3/00
[52] U.S. Cl. .................................................. 433/6; 128/860
[58] Field of Search .................................. 433/6; 128/848, 128/859, 860, 861, 862

[56] References Cited

U.S. PATENT DOCUMENTS

| | | | |
|---|---|---|---|
| 3,871,370 | 3/1975 | McDonald | 128/860 |
| 4,715,368 | 12/1987 | George | 433/6 |
| 4,718,662 | 1/1988 | North | 128/860 |
| 4,784,605 | 11/1988 | Bergersen | 433/6 |
| 5,092,346 | 3/1992 | Hays et al. | 128/848 |
| 5,117,816 | 6/1992 | Shapiro et al. | 128/848 |
| 5,513,656 | 5/1996 | Boyd, Sr. | 433/6 |

*Primary Examiner*—Nicholas D. Lucchesi
*Attorney, Agent, or Firm*—Seed and Berry LLP

[57] ABSTRACT

An apparatus for relieving upper airway disorders and related problems is shown and described. A tongue positioning extension is provided on a dental orthotic, the extension being positioned under a user's tongue on either side of the user's mouth. The extension is configured to elevate a tongue of the user, the tongue resting on an upper surface of the extension. The extension has a sufficient depth to prevent the tongue from moving below the extension, but is sufficiently narrow to prevent the extension from impinging on the tissues of the floor of the mouth. An upper surface of the extension is convex and polished, and edges of the extension are rounded, to allow the tongue to move easily and comfortably to the upper surface. By elevating the tongue in this manner, restriction of the upper respiratory passages is relieved, resulting in a variety of benefits to the user.

8 Claims, 2 Drawing Sheets

APPARATUS FOR RELIEVING UPPER AIRWAY DISORDERS AND RELATED PROBLEMS

TECHNICAL FIELD

This invention relates to dental orthotics, and more particularly, to an apparatus for elevating the tongue of a user to alleviate a variety of problems.

BACKGROUND OF THE INVENTION

A significant percentage of the population suffers from upper airway disorders. Such disorders generally involve airway restriction, and include, among other things, Obstructive Sleep Apnea Syndrome (OSAS), which causes a person to stop breathing, and Upper Airway Resistance Syndrome.

Traditionally, medical management of these problems has focused on the identification and use of air pressure devices during sleep to reduce breathing obstructions. More recently, airway orthotics have been used in the treatment of OSAS. Such orthotics function by pulling the lower jaw forward and open to allow movement of the tongue forward away from an airway obstructing position. Such orthotics are considered effective in the treatment of low level to moderate OSAS. Applicant believes, however, that there is a need in the art for an improved apparatus for relieving upper airway disorders and related problems.

SUMMARY OF THE INVENTION

Briefly, the present invention provides an improved apparatus for relieving upper airway disorders and related problems. In a preferred embodiment, a dental orthotic is provided, having a first side portion adapted to engage at least one mandibular tooth on the right side of a user's mouth, and a second side portion adapted to engage at least one mandibular tooth on the left side of the user's mouth. A tongue positioning extension is provided below the two side portions of the dental orthotic, the extension being configured to elevate the tongue of the user as the orthotic moves the tongue forward. The extension rests in the user's mouth under the tongue preferably in the region on either side of a user's mouth containing the mandibular second bicuspid and first molar. The extension may be provided on any conventional orthotic, such as a mandibular orthotic or a sleep apnea orthotic. Alternatively, the extension may be provided in any manner that allows it to be secured in a selected position in the user's mouth.

The extension is configured such that the depth of the extension is sufficient at a posterior portion to prevent the tongue from moving below the extension, but is sufficiently small to prevent the extension from impinging on the tissues of the floor of the user's mouth and the tissues of the tongue base, or from inhibiting forward motion of the tongue. In a preferred embodiment, the inner posterior and anterior surfaces of the extension engaged by the tongue are convex, and the edges of the extension are rounded to allow the tongue to move comfortably to the upper surface of the extension. To further facilitate the comfort of the user, the upper surface of the extension engaged by the tongue is polished.

The extension of the present invention acts directly on the underside of the tongue of a user, elevating the tongue and causing the tongue to move to an upward position resting on the extension. By doing so, an appropriate volume of the tongue is positioned in the oral cavity above the extension to relieve upper airway restrictions behind the oral cavity. It is believed that use of the apparatus provided in accordance with the present invention may also result in other benefits.

DETAILED DESCRIPTION OF THE INVENTION

Figure 1:
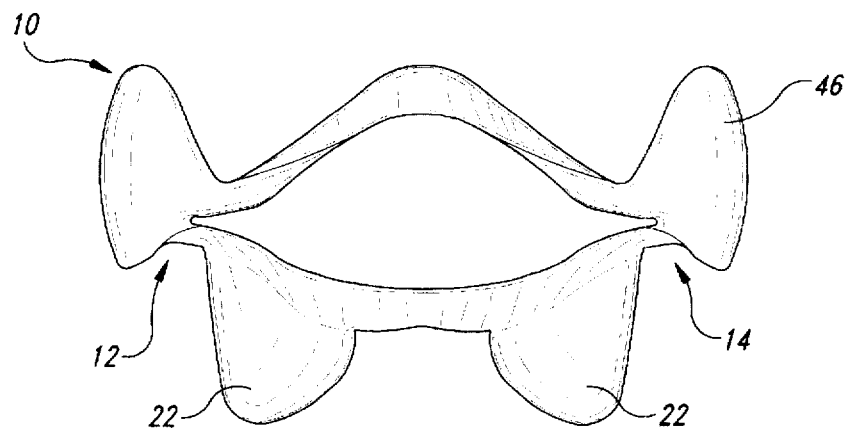
FIG. 1 is a front elevational view of an apparatus provided in accordance with a preferred embodiment of the present invention.
Figure 3:
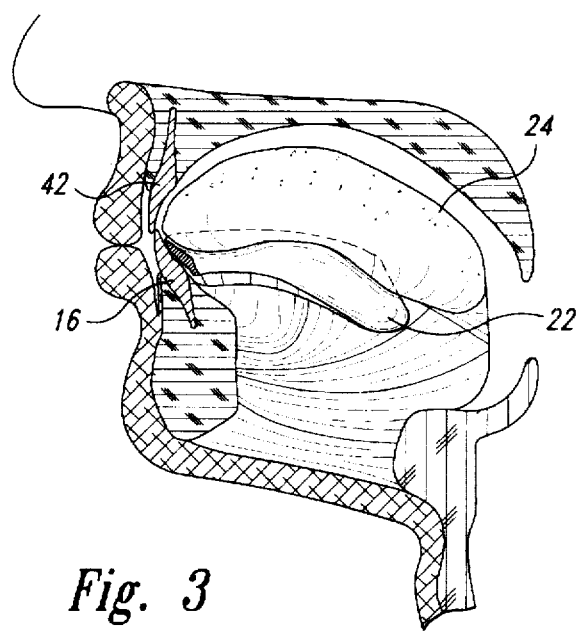
FIG. 3 is a cross-sectional elevational view of the apparatus illustrated in FIG. 2 in operative position, showing the location of the user's tongue.

An apparatus 10 provided in accordance with a preferred embodiment of the present invention for elevating the tongue of a user, is illustrated in FIG. 1. In a preferred embodiment, the apparatus is a dental orthotic having a first side portion 12 adapted to couple to at least one mandibular tooth 16 on a first side 18 of a user's mouth, the dental orthotic 10 having a second side portion 14 adapted to couple to at least one mandibular tooth 16 on a second side 20 of the user's mouth. A tongue positioning extension 22 is provided below the first side portion 12 and the second side portion 14, a shape of the extension being selected to elevate a tongue of the user. As illustrated in FIG. 3, the user's tongue 24 rests on an upper surface 26 of the extension 22.

Figure 2:
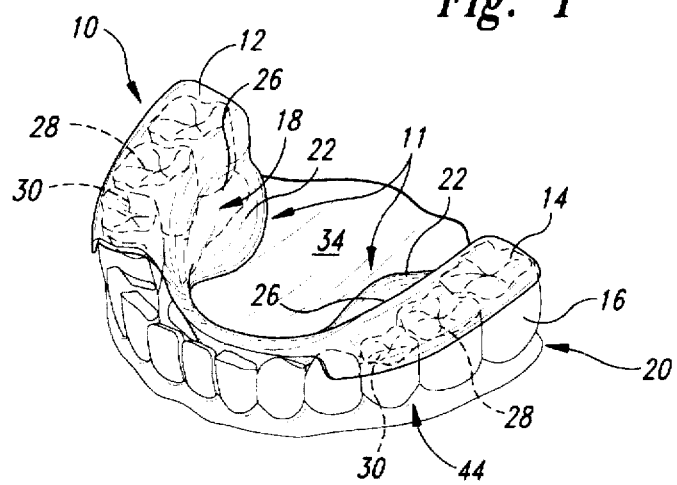
FIG. 2 is an isometric view of an apparatus provided in accordance with an alternative embodiment of the present invention and shown mounted on the lower jaw of a user.

In a preferred embodiment, as illustrated in FIG. 2, the inner sides 11 of the tongue positioning extension have a convex contour at a central region, which when positioned beneath the tongue, elevate and move the tongue forward. Although the exact location of the extension may vary from user to user, for most users, the greatest contour of the extension, when viewed from a top plan view, occurs at the junction of the mandibular second bicuspid 30 and first molar 28.

In a preferred embodiment, the extension is made of plastic and molded as an addition to a conventional orthotic device which is molded to fit selected teeth of the user, depending on the intended purpose of the orthotic. For example, the extension may be provided on a mandibular orthotic 44 as illustrated in FIGS. 2 and 3, or it may be provided on an orthotic that is configured to engage both the upper teeth 42 and lower teeth 16, for example a sleep apnea orthotic 46 as illustrated in FIG. 1. It will be understood, however, that the extension 22 may be provided in any manner that allows it to be positioned in the user's mouth in a desired location.

Figure 4:
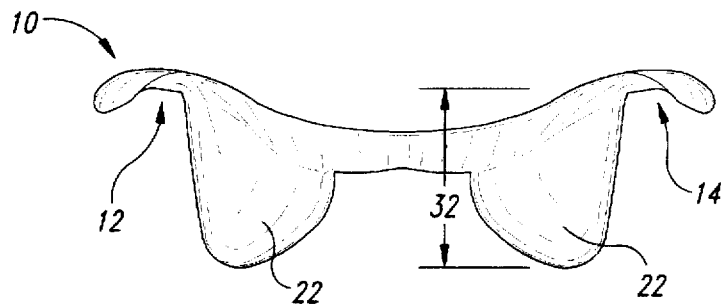
FIG. 4 is a front elevational view of the apparatus illustrated in FIG. 2.
Figure 5:
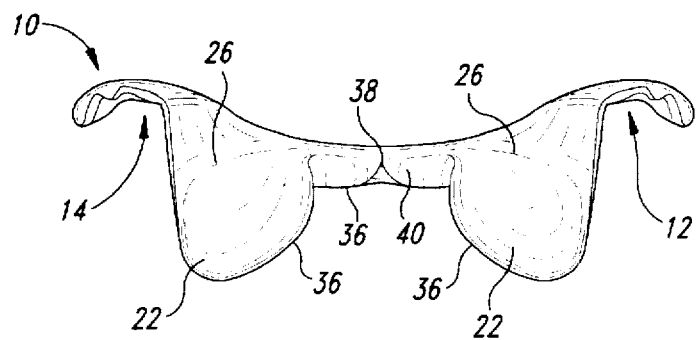
FIG. 5 is a rear elevational view of the apparatus illustrated in FIG. 2.

As illustrated in FIGS. 4 and 5, the shape and depth 32 of the extension 22 is such as to prevent the tongue from moving below the extension. The depth 32 is sufficiently small to prevent the extension from impinging on the tissues of the floor 34 of the mouth. In this manner, the extension allows for tongue movement, and the user is able to swallow without impingement or discomfort. Although the depth 32 of the extension may vary from user to user, it usually falls within the range of 8–25 mm and averages about 12 mm. Furthermore, the extension is contoured to ensure that it does not impinge on the lateral surface of the tongue.

In a preferred embodiment, as illustrated in FIGS. 4 and 5, the upper posterior surface 26 of the extension is convex to allow the tongue 24 to move easily to a position above the uppermost convex portion of the extension and to allow an appropriate volume of the tongue to be positioned in the oral cavity above the extension to ensure that the tongue does not restrict the user's airways 11. The edges 36 of the extension 22 are rounded to allow the tongue to move comfortably to the upper surface of the extension. To further ensure the comfort of the user, the upper surface 26 is polished. As illustrated in FIG. 5, a recess 38 is provided in an inner, anterior surface 40 of the connecting material between the extensions, the recess being adapted to accommodate the mandibular lingual frenum of the user.

Figure 6:
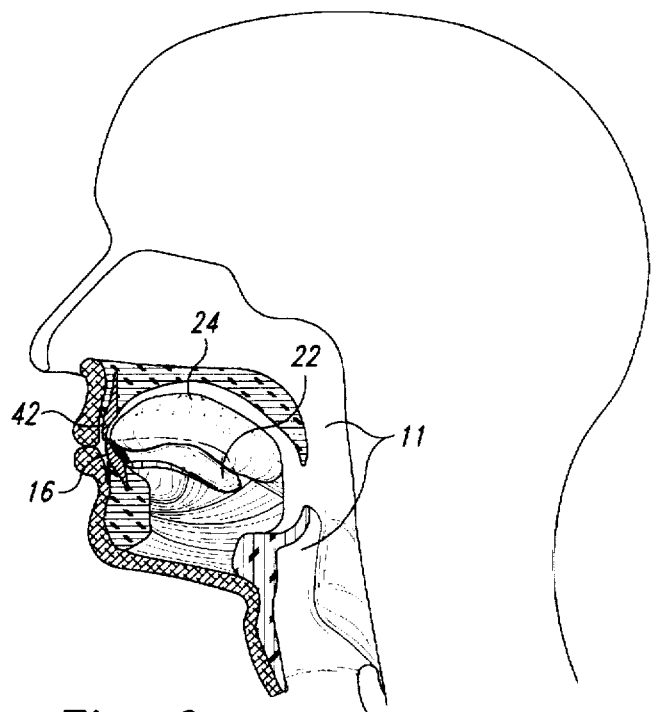
FIG. 6 is a cross-sectional elevational view of a user illustrating the oral cavity and respiratory passages.

An apparatus provided in accordance with the present invention therefore acts to support the tongue in an elevated, forward position. As illustrated in FIG. 6, such an elevated, forward position for the tongue prevents the tongue from blocking the upper respiratory airway passages 11 of a user. While it may be useful to prevent such airway restrictions during sleep, it may also be beneficial to alleviate this condition during the day. This may be best achieved by providing the extension on a device that couples only to the mandibular teeth, as illustrated in FIG. 2.

Use of a device provided in accordance with the present invention may result in a variety of benefits related to an airway restriction problem. For example, applicants believe that a person suffering from an upper airway irregularity may tend to carry their head in a forward position and have muscle contraction problems, resulting in headaches, muscle aches, etc. However, when the tongue is elevated and moved forward in accordance with the present invention, the user corrects his or her posture and thereby prevents the related previously experienced aches or other discomfort.

An apparatus for relieving upper airway disorders and related problems has been shown and described. From the foregoing it will be appreciated that although embodiments of the invention have been described herein for purposes of illustration, various modifications may be made without deviating from the spirit and scope of the invention. Thus, the present invention is not limited to the embodiments described herein, but rather is defined by the claims which follow.

I claim:

1. An appliance for elevating the tongue of the user comprising:

a dental orthotic having a first side portion adapted to couple to at least one mandibular tooth on a first side of a user's mouth, a second side portion adapted to couple to at least one mandibular tooth on a second side of the user's mouth, and a tongue positioning extension joined to said portions and having a pair of laterally spaced tongue positioning portions extending downwardly and toward one another from said side portions, the shape of said tongue positioning portions being such as to jointly elevate the tongue of a use and to allow the tongue to rest on an upper surface of the extension, said tongue positioning portions having smooth tongue engaging and supporting surfaces, the depth of the extension at said tongue positioning portions being such as to prevent the tongue from moving below the extension and impinging on the tissues of the floor of the mouth.

2. The apparatus according to claim 1 wherein the depth of the extension is 8–25 mm.

3. The apparatus according to claim 1 wherein edges of the extension are rounded to allow the tongue to move comfortably to the upper surface of the extension.

4. The apparatus according to claim 1 wherein a recess is provided in an anterior surface of the extension at the center thereof to accommodate a mandibular lingual frenum of the user.

5. The apparatus according to claim 1 wherein the upper surface of the extension is polished.

6. The apparatus according to claim 1 wherein the dental orthotic is a mandibular orthotic.

7. The apparatus according to claim 1 wherein the dental orthotic is an upper airway orthotic.

8. The apparatus according to claim 1 wherein the dental orthotic is adapted to matingly engage upper and lower teeth of the user.

* * * * *